United States Patent [19]

Nobbio

[11] Patent Number: Plant 5,765

[45] Date of Patent: Jul. 15, 1986

[54] CARNATION NAMED BUGGIO

[76] Inventor: Giacomo Nobbio, Strada Villetta 5, San Remo, Imperia, Italy

[21] Appl. No.: 600,849

[22] Filed: Apr. 16, 1984

[51] Int. Cl.[4] ..... A01H 5/00

[52] U.S. Cl. ..... Plt./70

[58] Field of Search ..... Plt./70–73

*Primary Examiner*—James R. Feyrer

*Attorney, Agent, or Firm*—Charles W. Rummler

[57] ABSTRACT

A new variety of carnation plant distinguished by its flowers of bright yellow color, the petals of which are streaked with cyclamen-red, the flowers being of a double type and of very large size carried on long, strong stems of normal character and the flower having good endurance as a cut flower and excellent suitability for shipment.

1 Drawing Figure

BACKGROUND OF THE NEW PLANT

This new carnation cultivar was originated in 1978 as a seedling resulting from my crossing of the variety known as "Raggio di Sole" (i.e., "Ray of Sunlight") as the seed parent, which has a flower that is orange in color and is identified in my records under U.S. Plant Pat. No. 8,739, with an unnamed variety identified in my records under U.S. Plant Pat. No. 8,763, which has a flower that is yellow in color. This crossing was done by me at my breeding establishment in San Remo, Italy, with the object of producing an improved carnation variety particularly suitable for commercial propagation and the production of cut flowers. Reproduction of this new plant was done by means of cuttings from the original seedling and continued propagation under conventional greenhouse conditions through successive generations has demonstrated conclusively that the novel characteristics of the new plant hold true from generation to generation and appear to be firmly fixed.

DESCRIPTION OF THE DRAWING

My new carnation cultivar is illustrated by the accompanying full color photographic drawing, which shows the inflorescence of a fully grown plant, the view including buds in various stages of opening, a face view of a fully developed flower, together with specimens of the flower stem and specimens of the flower petals, the color rendition being as nearly true as it is reasonably possible to obtain by means of conventional photographic procedures.

DESCRIPTION OF THE NEW PLANT

The following is a detailed description of my new carnation variety based upon observation of plants grown under conventional greenhouse procedures, the color designations being according to The R.H.S. Colour Chart published by The Royal Horticultural Society of London, England.

THE PLANT

Origin: Seedling.

Parentage:

*Seed parent.*—A variety known as "Raggio di Sole" identified in the records of my breeding establishment under U.S. Plant Pat. No. 8,739.

*Pollen parent.*—An unnamed variety identified in the records of my breeding establishment under U.S. Plant Pat. No. 8,763.

Classification:

*Botanic.*—*Dianthus caryophyllus.*

*Commercial.*—Greenhouse carnation.

Form: Herbaceous with long stems having seven internodes visible immediately under the calyx.

*Stem color.*—Medium Green.

*Stem size.*—Of medium thickness with rounded cross-section in the middle of the longest internode.

Growth: Vigorous and upright with moderate strength. The initial stem arising from a rooted cutting is pinched at about 10 cm. from the base after the stem has reached a height of about 30 cm. This is done to promote the rapid growth of lateral shoots each of which develops as a sturdy upright stem which ultimately produces a flower at its terminal end. Each stem produces a medium number of branches each of which is capable of flowering at its terminal end and each main stem may be pruned according to the desired length for the terminal flower or the branches may be allowed to flower normally according to the stem length desired.

Branching: Medium.

Foliage:

*Quantity.*—Sparse.

*Leaf size.*—Short in length and of medium breadth.

*Leaf shape.*—Linear and curled with entire margins and acuminate apex.

*Texture.*—Smooth.

*Color.*—Green.

THE BUD

Size: Large.

Shape:

*As the sepals begin to divide.*—Cylindrical, becoming ovoid as the color appears.

Sepals:

*Condition.*—Upstanding and very firm at the base of the calyx.

Calyx:

*Shape.*—Bell-shaped.

*Length.*—Medium.

*Splitting.*—The calyx does not split.

*Aspect.*—Smooth.

Peduncle: Rigid and erect.

*Color.*—Grey-Green; somewhat darker than that of the calyx.

THE FLOWER

Blooming habit: Continuous.
Size of bloom: Very large and of double type.
Borne: Singly on strong, upright stem.
Shape: Symmetrical with slightly flattened cupule at full bloom.
Petalage:
*Number of petals.*—More than 80.
*Arrangement.*—Generally imbricated.
*Shape.*—Fan-shaped with slightly fringed margin.
*Color.*—Yellow, between R.H.S. 10C and 12C, longitudinally streaked with Cyclamen Red, R.H.S. 55A.
*Texture.*—Soft.
*Appearance.*—Satiny.
Fragrance: Very weak.
Persistence: The flowers hang on and dry.
Lasting quality: Good endurance as a cut flower and good suitability for shipment.

REPRODUCTIVE ORGANS

Androecium: Absent during the winter period.
Styles:
*Number.*—More than two.
Stigma: Surface is smooth.
Ovary:
*Shape.*—Ovoid.

This new carnation variety has well blended and stable characteristics and is clearly distinguished from other commercially available varieties by the size and coloration of its flowers. This variety is most similar to its seed parent "Raggio di Sole" but differs particularly by the fact that the ground coloration of the flower of the present variety is paler and the variegation is more pronounced; and by the fact that the flower as a whole is larger than that of the seed parent.

I claim:

1. A new and distinct carnation cultivar, substantially as herein shown and described, characterized by its very large flower of basically yellow color and having petals bearing thin, longitudinal streaks of cyclamen red color, the flowers being very large and of a double type.

* * * * *

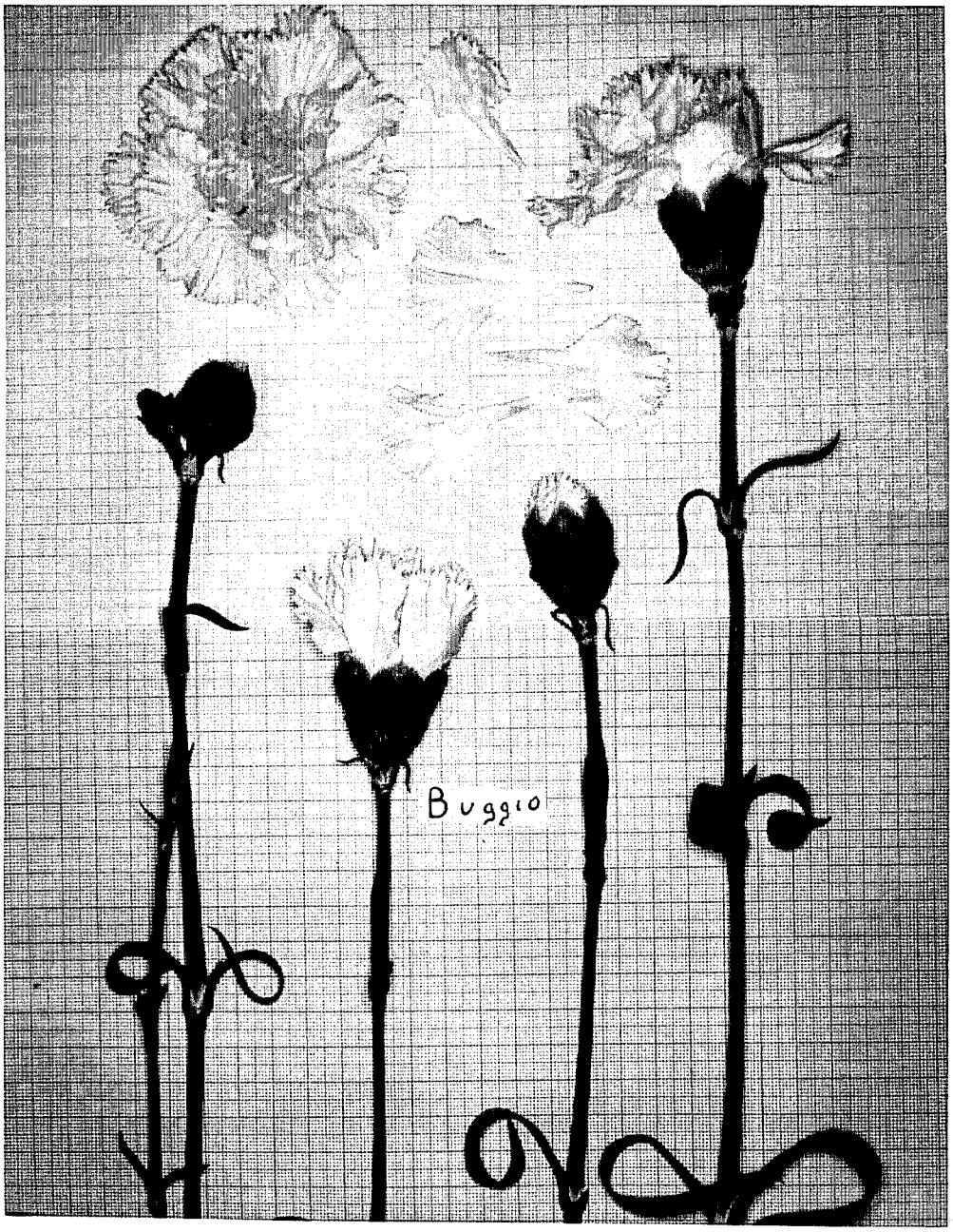
Buggio

UNITED STATES PATENT AND TRADEMARK OFFICE

CERTIFICATE OF CORRECTION

PATENT NO. : PP 5,765

DATED : July 15, 1986

INVENTOR(S) : Giacomo Nobbio

It is certified that error appears in the above-identified patent and that said Letters Patent are hereby corrected as shown below:

Column 1, line 7, delete "U.S. Plant".

Column 1, line 8, delete "Pat.".

Column 1, line 49, delete "U.S. Plant Pat.".

Column 2, line 3, delete "U.S. Plant Pat.".

Signed and Sealed this

Ninth Day of June, 1987

*Attest:*

*Attesting Officer*

DONALD J. QUIGG

*Commissioner of Patents and Trademarks*